United States Patent [19]

Snyder

[11] 4,197,288
[45] Apr. 8, 1980

[54] NEUROLEPTIC RADIORECEPTOR ASSAY METHOD AND KIT

[75] Inventor: Solomon H. Snyder, Baltimore, Md.

[73] Assignee: Burroughs Wellcome Co., Research Triangle Park, N.C.

[21] Appl. No.: 845,554

[22] Filed: Oct. 26, 1977

Related U.S. Application Data

[63] Continuation-in-part of Ser. No. 828,537, Aug. 29, 1977, abandoned, and a continuation-in-part of Ser. No. 759,985, Jan. 17, 1977, abandoned.

[51] Int. Cl.$^2$ ............... G01N 33/16; A61K 43/00; B65D 81/32
[52] U.S. Cl. ............................. 424/1; 23/230 B; 206/569; 424/12
[58] Field of Search ............ 424/1, 12; 23/230 B, 23/259; 206/569

[56] References Cited

PUBLICATIONS

Enna et al., Nature, vol. 263, No. 5575, Sep. 23, 1976, pp. 338–341.
Enna et al., J. of Neurochem., vol. 26, 1976, pp. 221–224.
Snyder et al., Psychopharmacology Comm., vol. 1, No. 6, 1975, pp. 663–673.
Creese et al., Life Sciences, vol. 17, 1975, pp. 993–1002.
Seeman et al., Nature, vol. 261, Jun. 24, 1976, pp. 717–719.
Garnett et al., Radiopharmaceuticals and Labeled Compounds, vol. 1, IAEA, Viena, 1973, pp. 405–410.

*Primary Examiner*—Benjamin R. Padgett
*Assistant Examiner*—Christine M. Nucker
*Attorney, Agent, or Firm*—Donald Brown

[57] ABSTRACT

Method, composition of matter and kit for determining the concentration of neuroleptic drug(s) in an animal or human patient's body fluid e.g., blood serum, blood plasma, urine, saliva, spinal fluid, etc., which comprises combining the patient's body fluid with dopamine receptor material and radioactive dopamine receptor binder and then measuring the percent inhibition of binding of the radioactive binder by the drug in the patient's fluid. The kit for performing the above method includes dopamine receptor material and radioactive dopamine receptor binder.

29 Claims, 3 Drawing Figures

NEUROLEPTIC RADIORECEPTOR ASSAY METHOD AND KIT

This application is a continuation in part of U.S. patent application Ser. No. 759,985 filed Jan. 17, 1977, abandoned, and 828,537 filed Aug. 29, 1977, now abandoned.

BACKGROUND OF THE DISCLOSURE

Neuroleptic drugs represent a wide range of psychotropic agents, sometimes also referred to as the major tranquilizers. The two most common subclasses of neuroleptic drugs are the phenothiazines and butyrophenones. These drugs are prescribed extensively throughout the world for the treatment of schizophrenia, the relief of certain forms of depression, and as antiemetics. Dosage requirements can vary widely among different patients. In part the variable dose requirement is related to marked differences in uptake of the drug among various individuals.

It is generally felt that a simple and sensitive technique to measure neuroleptics in blood and other body tissues would greatly facilitate selection of optimal doses or a particular drug for individual patients. This is important in ensuring that patients have adequate blood and brain levels to attain therapeutic effects and also to make sure that a patient does not receive a higher dose of the drug than is necessary for treating his or her symptoms.

Long term treatment with high doses of these drugs is sometimes associated with abnormal motor movements referred to as tardive dyskinesia, a disfiguring and frequently permanent side effect.

Detecting neuroleptic levels in body fluids ideally should employ a technique which can be used with all neuroleptics. Moreover, because frequently metabolites of the parent drug have therapeutic activity, an ideal method should be able to measure pharmacologically active but not inactive metabolites in addition to the parent drug.

Presently available techniques, such as gas-liquid chromatography, cannot be applied routinely in clinical laboratories because they are quite costly and very time consuming. Moreover these techniques are applicable only for individual drugs rather than for the whole class of neuroleptics. Such prior art methods also do not specifically detect active metabolites.

A variety of indirect evidence accumulated since about 1962 had suggested that the therapeutic actions of neuroleptic drugs in schizophrenic patients involved a blockade of receptor sites for dopamine in the brain. In none of these investigations had researchers been able to measure the dopamine receptor directly. Using $^3$H-haloperidol or $^3$H-dopamine a group of researchers succeeded in labeling the dopamine receptor so that it could be measured directly. See the publications Creese et al., LIFE SCIENCES, Vol. 17, pp 993-1002 (1975), Snyder et al., Psychopharmacology Communications, 1 (6), 663-673 (1975), Enna et al., NATURE Vol. 263, Sept. 23, 1976, pp 338-344, and Seeman et al., NATURE, Vol. 261, June 24, 1976 pp 717-719.

In these same investigations (see the above noted publications) it was shown that neuroleptic drugs do indeed compete for the binding of $^3$H-dopamine and $^3$H-haloperidol to the receptor sites in proportion to their clinical efficacy thus showing that the therapeutic actions of the drugs are associated with a blockade of dopamine receptors.

None of these publications of the dopamine receptor itself disclosed anything beyond the fact that the dopamine receptor can be measured with $^3$H-haloperidol and $^3$H-dopamine and that neuroleptic drugs inhibit the binding of the $^3$H-agents. Moreover the information contained in these above mentioned publications does not provide a tool for measuring amounts of neuroleptic drugs in body fluids of human patients, because a number of needed elements, all of which were yet to be discovered, had to be discovered to exist for a successful assay for levels of neuroleptic drugs. For a successful assay for neuroleptic drug levels it was necessary to discover the non-specific effects of body fluids on the binding properties of the dopamine receptor and discover means of reducing or abolishing them. It was also necessary to discover that neuroleptic drugs added to body fluids could be recovered in a form that would still interact with the dopamine receptor. It was also necessary to show that in the presence of body fluids increasing levels of neuroleptic would in a predictable fashion produce progressively greater blockade of dopamine receptors. Only after making a series of discoveries as disclosed herein which reduced nonspecific effects of body fluids on the dopamine receptor, permitted recovery of added neuroleptics and resulted in reproducible augmentations in receptor blockade with increasing amounts of neuroleptics in body fluids was it possible to measure neuroleptic drugs in body fluids with this invention.

One study (Enna and Snyder *J. Neurochem.*, 1976 26: 221-224) coauthored by the present inventor would on its face appear to be relevant to the present invention. This publication discloses the use of a GABA receptor as a means to measure GABA itself in brain tissue. However, this method can only be used for GABA, because neuroleptic drugs do not bind with appreciable potency to the GABA receptor. In competing for binding to the GABA receptor, major neuroleptic drugs are less than 1/1000th as potent as GABA so that circulating levels of neuroleptics could not be detected at all. Because of the limited sensitivity of the GABA radioreceptor assay, one would not expect an assay using another receptor to detect the low levels of neuroleptics which occur in the body fluids of patients. Moreover, in actual clinical practice the most important body fluid for measuring drugs is blood. Plasma proteins in the blood prevent binding of GABA to its receptor so that on the basis of the GABA assay one would not expect to be able to measure GABA or drugs in blood using the GABA receptor or any other receptor.

The present invention departs from the above in that it has been discovered that it now is possible to detect neuroleptic drugs with sensitivities thousands of times greater than achieved with the GABA assay in blood plasma and other body fluids. The GABA receptor does not have sufficient affinity for any known drug used in patients to permit their assay. Thus the GABA assay is restricted to the measurement of GABA itself, a neurotransmitter contained in the brain, but cannot be used to measure any clinically employed drug.

It is also believed that drugs which are not neuroleptics do not bind to the dopamine receptor sites.

BRIEF DESCRIPTION OF THE DISCLOSURE

The present invention is directed to a new technique which permits rapid determination of the concentration of neuroleptic drugs in patients. The making of this determination is obviously quite important since in most patients a certain preestablished concentration is necessary to obtain the desired medicinal effect. However, while the desirable concentration of neuroleptic in the patient's blood is known, it has been found that the uptake of neuroleptics by most patients is quite variable and thus one has no assurance that a certain dose of neuroleptic administered to the patient will produce the desired concentration in the blood. The prior art techniques for measuring the concentration of neuroleptics as mentioned previously are quite time consuming and expensive and accordingly a new and improved technique that could easily and rapidly be used was needed to insure that the patients were being properly dosed to achieve the beneficial results without causing harmful side effects.

The present invention provides such a technique and is in part based upon the discovery that a neuroleptic drug contained in the body fluid e.g., blood of a patient (human) will successfully compete with the binding of radioactive dopamine receptor site binder(s) to dopamine receptor sites of dopamine receptor material in a manner that an accurate determination of neuroleptic drug concentration can readily be determined.

The present invention is also based in part upon the discovery that once the competition of the binder and drug to the dopamine receptor has proceeded for the desired time, free dopamine receptor material having bound to it, drug and binder can be successfully separated from free drug and binder and bodily fluids without destroying the accuracy of the concentration measurement to be made.

After separation, the level of radioactive dopamine receptor binder may be measured in a conventional radioactivity measurement device e.g., gamma counter or scintillation counter depending on the radionuclide of the radioactive dopamine receptor binder, and compared with standard curves to determine the concentration of neuroleptic drug in the patient.

Thus there is described herein a method for measuring levels of neuroleptics in patients based on the ability of neuroleptics to compete with the binding of radioactive binders (ligands) including dopamine agonists or antagonists to dopamine receptor sites of dopamine receptor material.

In this procedure increasing amounts of neuroleptic drug or active metabolites thereof decrease the binding of the radioactive labelled binder to the dopamine receptor material. The biological body fluid sample may be assayed without separation of the neuroleptic drug therefrom e.g., blood plasma or blood serum may be directly assayed to determine the neuroleptic drug levels.

The source of dopamine receptor material can be any dopamine receptor materials obtained from animal tissues enriched in dopamine receptors including the caudate, putamen of brain, the kidney and the superior cervical ganglia. Suitable receptor material is obtained from humans or from animal species such as bovine, porcine, rodent, ovine or birds.

From a practical standpoint one of the most readily available dopamine receptor material is calf brain which can be readily obtained from slaughterhouses.

The dopamine receptor material may be used as such or fractionated in a conventional manner to provide fractions enriched in synaptic membranes and may be washed or unwashed.

The dopamine receptor material may preferably be sold as a conventional freeze dried preparation in a test tube e.g., coupled to the interior of a test tube so that binder and drug may be easily added to it.

As the radioactive dopamine receptor binder, radioactive labelled compounds such as haloperidol, pimozide, chlorpromazine, flupenthixol, spiroperidol, clozapine, thioridazine, trifluoperazine, fluspirilene, clopenthixol, loxapine, perphenazine, dopamine, apomorphine, analogs of dopamine and others having the dopamine receptor binding properties exhibited by these compounds may be used.

In principal these compounds are conventionally labelled in the manner well known in the prior art with any radionuclide. A listing of the radionuclides which are now conventionally in use in reagents and which may be used in this invention are listed in the index of Radionuclides found on page 80 of the 1975 Catalog of New England Nuclear Corporation, Boston, Massachusetts, U.S.A. ©New England Nuclear 1974. Among radionuclides which are preferred in this invention, the following may be mentioned: hydrogen −3 (tritium) and the radiosotopes of iodine ($^{123}I$, $^{124}I$, $^{125}I$, $^{126}I$, $^{128}I$, $^{130}I$, $^{131}I$, and $^{132}I$) with $^{125}I$ and $^{131}I$ being the preferred from considerations of availability, half life and specific activity and the ability to radioactive Iodine compounds to be readily counted using a conventional gamma counter usually available in hospitals and sold by Packard Instruments or others.

In a typical experiment the membranes (dopamine receptor material can be incubated at various temperatures for various periods of time with appropriate ligand (dopamine receptor binder). Typically [$^3$H]benperidol of high specific radioactivity purchased from New England Nuclear of Boston, Mass. is incubated with calf caudate membranes in a buffer solution preferably at a pH of 6 to 9 at 37° for 10 mins and then filtered under vacuum through Whatman GF/B filters with two 5 ml rinses of cold buffer. The filters can be counted in liquid scintillation counters e.g. Packard Instrument auto gamma scintillation spectrometer model 5260. Specific binding to the dopamine receptor is determined as the excess over blanks taken in the presence of 1 $\mu$M dopamine or 10 $\mu$M (+)-butaclamol, though blank values can be obtained using a variety of other agents that bind to the dopamine receptor. The ligand can be any dopamine agonist or antagonist or mixed agonist-antagonist labeled with radioactivity.

Biological fluid samples, e.g., urine blood plasma, blood serum, etc., supposedly containing neuroleptics are added to these assays.

The biological samples, e.g., blood plasma, or blood serum can be added without any purification.

The neuroleptics may be purified or concentrated by any of numerous chemical techniques including solvent extraction, column chromatography, adsorption onto specially treated fibers or other chemical substances, or by any other chemical procedure which may help purify the neuroleptic or concentrate it. The amount of neuroleptic is quantified by the extent to which it decreases binding of the labeled ligand to the dopamine receptor. The values can be quantified in any convenient units. The incubation mixture for the receptor binding can include any of numerous additives to facilitate binding or to protect the drugs or labeled liquids. The duration of the incubation and its temperature can vary and involve any convenient period, though it is usually best to conduct the incubation to equilibrium e.g. suitable time for incubation could be anywhere from 2 minutes to 4 hours. Receptor bound ligand can be trapped by filtration, centrifugation or any other known techniques which separates bound from unbound ligand.

It should also be understood that other suitable filter material may also be used so long as it will permit the retention of the large sized dopamine receptor material having bound radioactive binder and neuroleptic drug while being able to separate the unbound radioactive binder (ligand) and free neuroleptic drug. Other examples of suitable filter material include Millipore filters of various sizes e.g. 0.6 micron diameter holes.

Preferably the dopamine receptor material is buffered by a buffering solution such as Tris-HCl buffer sold by Sigma Labs., St. Louis, Mo., having a pH of 7.7. Other suitable buffering solutions include sodium phosphate buffer, Glycine buffer and HEPES buffer and others which will provide the preferred pH (6 to 9) in the mixture to permit rapid binding of the radioactive labelled binder and the neuroleptic drug to the dopamine receptor material.

Thus this invention provides a new and improved method for determining concentration in humans of neuroleptic drugs such as haloperidol, pimozide, chlopromazine, fluphenazine, flupenthixol, spiroperidol, clozapine, thioridazine, trifluoperazine, fluspirilene, chopenthixol, loxapine, and others which are known in this art as competitors of dopamine.

In particular the method is easily practiced by preparing a mixture of radioactive binder, blood fluid, e.g., blood serum, blood plasma or urine, and dopamine receptor material, measuring the radioactivity (counts) of the binder attached to the dopamine receptor material preferably after separating unbound materials (e.g., blood serum or plasma, binder, drug, if present, etc.) from the dopamine receptor material and then deriving the concentration of the neuroleptic drug from a standard curve which indicates the concentration of neuroleptic drug vs. inhibition of the radioactive binder binding to the dopamine receptor material caused by the neuroleptic drug in the blood serum or plasma.

It has been discovered that the concentrations of bodily fluids such as blood plasma or blood serum in the assay is most preferably no greater than about 15% of the total assay volume of ingredients in the test tube. Concentrations of plasma or serum in excess of about 15% inhibit markedly binding of $^3$H-ligands to the dopamine receptor even without any drug present. Optimally the concentrations value should be about 10% or less. Concentrations in excess of about 15% may effect the validity of the assay test results. As used herein the total assay volume assay ingredients means the sum of ingredients in the test tube and the like prior to washing and adding scintillation fluid.

It is at this time preferred that the amount of bodily fluids e.g., blood plasma and blood serum used in the test be greater than about one microliter, however this amount is not critical and may change as improved instrumentation or manipulative techniques are developed.

In addition this invention provides a new composition of matter comprising radioactive binder, neuroleptic drug and dopamine receptor material and blood serum or plasma and a kit container comprising the ingredients for performing the technique described herein.

Figure 1:
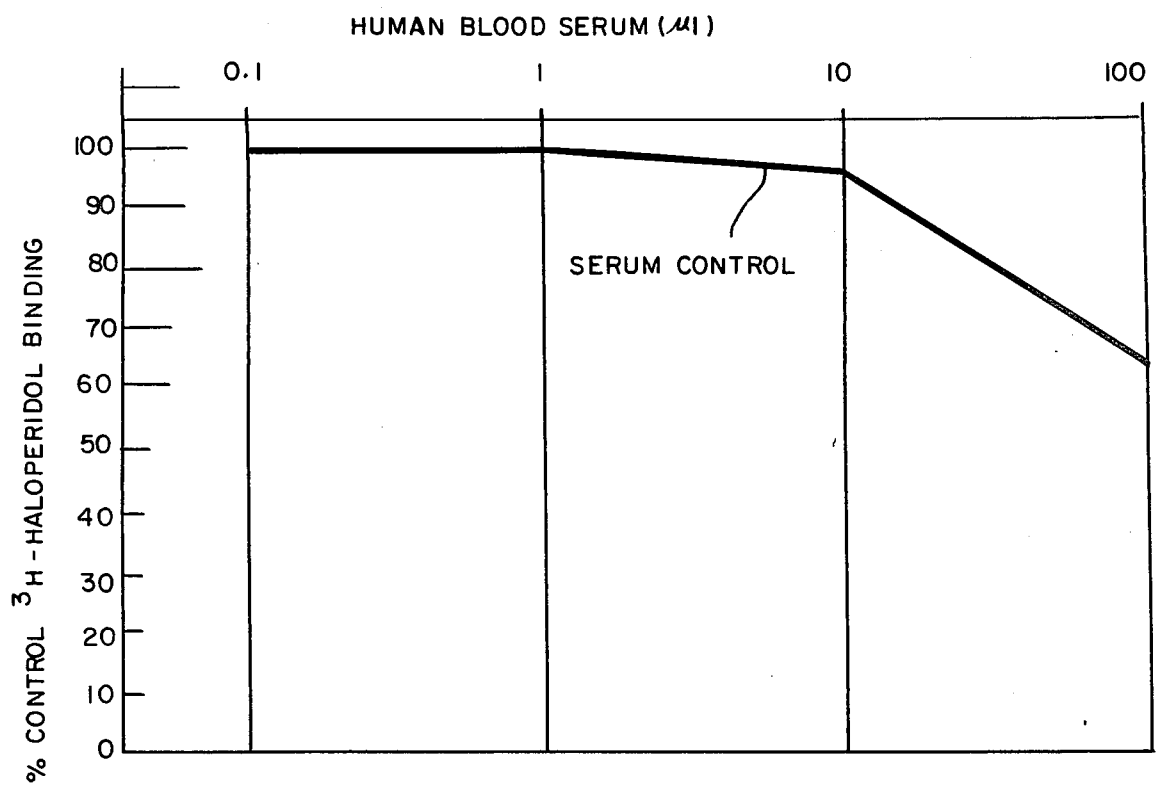
FIG. 1 is a graph showing the effect of human serum on $^3$H-Haloperidol binding for Example I.

The following examples illustrate the invention.

EXAMPLE I

To each of triplicate groups of nine test tubes, there was added 1.8 milliliters of dopamine receptor material (tissue preparation) comprising rat striatum prepared by method of Creese et al., Vol. 17, pp 993-1002 Life Sciences published by Pergamon Press and 10,000 cpm of $^3$H-Haloperidol of Specific Activity 8.302 ci/mmol (obtained from New England Nuclear Corporation, Boston, Mass.) and various samples each of 100 μl in numbered test tube as follows:

Test Tube No.

(1) 100 μl of Tris-HCl buffer (pH 7.7 at 25° C.) (same buffer as disclosed in Creese et al., Vol. 17, Life Sciences pp 993-1002) with $10^{-5}$ (MOLAR) Haloperidol.

(2) 100 μl human blood serum (sold by K-N Enterprises of 7346 N. Montecello Avenue, Skokie, Illinois, U.S.A.).

(3) ten-fold dilution of said human serum using said Tris-HCl buffer.

(4) ten-fold dilution of the contents in test tube No. 3 in said Tris-HCl buffer as described.

(5) ten-fold dilution of the contents in test tube No. 4 in said Tris-HCl buffer as described.

(6) $10^{-5}$ M MOLAR) Haloperidol in 100 μl of human serum as described above.

(7) ten-fold dilution of the contents of test tube No. 6.

(8) ten-fold dilution of the contents of test tube No. 7.

(9) ten-fold dilution of the contents of test tube No. 8.

All samples were diluted by adding of said Tris-HCl buffer to a volume of 1 ml. All tubes were now incubated (to permit binding of Haloperidol and radioactive Haloperidol to the rat tissue) in water bath at 37° C. for ten (10) minutes. At the end of the ten minutes, the contents of each tube was filtered under vacuum through Whatman GF/B glass fibre filter as in Creese et al., Vol. 17, Life Sciences pp 993-1002). Filters were now washed two times with 5 ml ice cold Tris-HCl buffer (pH 7.7) Sigma Labs. Filters were now placed in scintillation vials with 1 ml of 1% sodium dodecyl sulphate solution and left for three hours at room temperature (20° C.). 10 mls of Brays Scintillant (New England Nuclear) were now added to each vial and tritium determined by scintillation counting using Packard Instruments Model 5260 Scintillation Counter.

FIG. I shows the inhibition of binding of $^3$H-Haloperidol on the rat brain preparation of this example caused by human blood serum based on the amount of human blood serum in μl.

FIG. II shows the inhibition of binding of $^3$H-Haloperidol, human blood serum and Haloperidol (standard non-radioactive dopamine receptor binder) at the various concentrations shown.

In order to determine the concentration of neuroleptic drug (e.g. Haloperidol) in the serum of a human patient, 100 μl of serum from such patient separated from whole blood (human) in a conventional manner would be assayed by doing the following: The 100 μl of serum is mixed and incubated with 20 μl of $^3$H-Haloperidol (10,000 cpm), 1.8 milliliters of the rat striatum preparation used in this example while in a test tube for 10 minutes at 37° C. Thereafter the contents of the test tube is filtered under vacuum through a Whatman GF/B glass fiber filter which was then washed twice with 5 ml ice cold Tris-HCl buffer (pH 7.7) as in this Example I. Thereafter, percent inhibition of $^3$H-Haloperiodol binding is determined by placing the washed filter in a scintillation vial with 1 milliliter 1 percent sodium dodecyl sulphate solution which is then left for three hours at room temperature (20° C.). Thereafter Bray's Scintillant (10 ml) is added and tritium determined using a scintillation counter as above.

The concentration of Haloperidol in the serum is then determined by reference to FIG. II standard curve. For example, if in the absence of patient's serum 10000 cpm of $^3$H-Haloperidol bound to the dopamine receptor material was measured and in the presence of a patient's serum 2000 cpm of $^3$H-Haloperidol was measured, this would indicate 80% inhibition by haloperidol drug from patient's serum.

The concentration of such drug in the patient's serum can then be directly read from the standard curve FIG. II. In this case the concentration of haloperidol drug equivalents in the serum would be approximately $6 \times 10^{-9}$ M which is the value obtained by reading the 20% control figure (80% inhibition) at the left hand axis as shown by the dotted line and then reading the haloperidol concentration from the bottom axis of FIG. II.

Using such information the physician will be able to ascertain if the drug level in the patient is within the desired therapeutic range.

Figure 2:
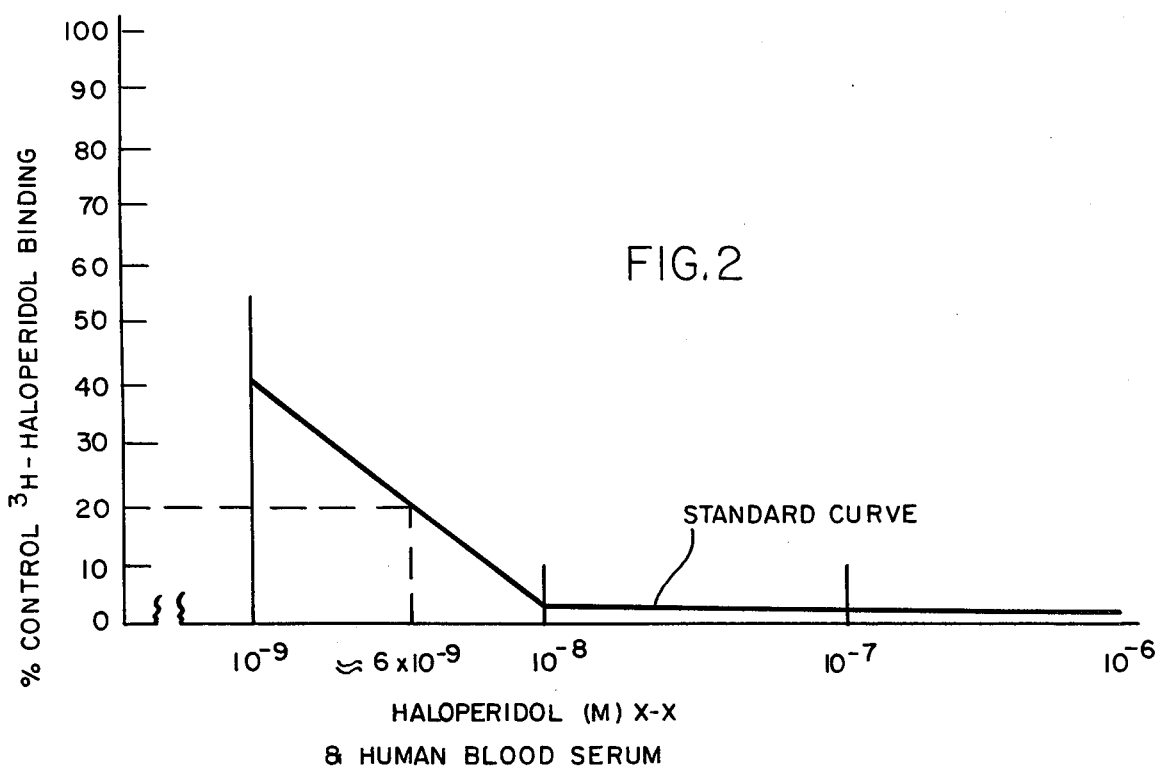
FIG. 2 is a graph showing the effect of Haloperidol, and human serum (from blood) on $^3$H-Haloperidol binding for Example I.
Figure 3:
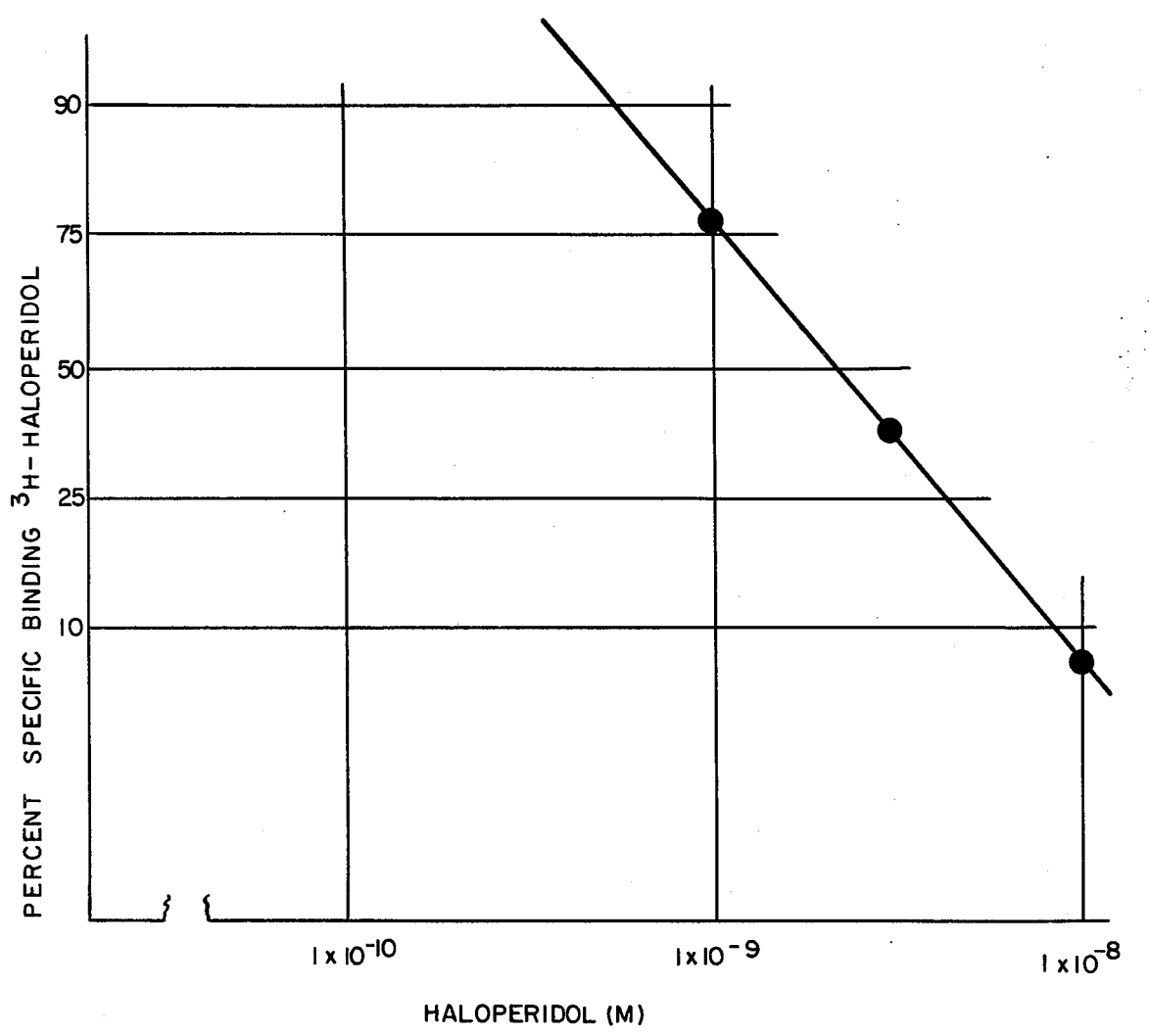
FIG. 3 is a graph showing the effect of Haloperidol on $^3$H-Haloperidol binding for Example II.

It should be understood that if the concentration of one of the neuroleptics previously mentioned is to be determined, then a standard curve as FIG. 2 would be obtained as disclosed herein in this example by combining the other drug e.g., pimozide with $^3$H-Haloperidol, serum and dopamine receptor material e.g., rat striatum. The results can obviously be expressed as pimozide equivalents, haloperidol equivalents, dopamine blocking capacity or any other way that pleases the user.

Thus it should be observed that a single radioactive dopamine receptor binder e.g., $^3$H-Haloperidol can be used to generate all standard curves.

EXAMPLE II

A. Procedure for extraction of neuroleptics from plasma.

Two ml blood plasma containing drug are added to 8 ml heptane with 5% isoamylalcohol in 15 ml glass conical extraction tubes and vortex for 10 seconds.

Add 0.1 ml 10 N NaOH. Then, pack the tubes in ice and shake on a mechanical shaker for 1 hour at moderate speed, and centrifuge at 1000 g. 10 minutes.

Remove 6 ml of the organic phase and add it to a tube containing 1.5 ml freshly prepared 0.1% ascorbic acid. Shake in a mechanical shaker for 1 hour, then centrifuge at 1000×g, 10 minutes.

Remove the organic layer entirely. The ascorbic acid is assayed straight, and with ascorbic acid dilutions of 1:3 and 1:10. An emulsion layer will often form between the ascorbic acid and the heptane. This can be reduced by placing extraction tube in warm water for a short period of time.

To determine the actual recovery of the specific drug from the extraction, 20 μl of $10^{-5}$ M drug are added to 2 ml drug-free blood plasma, giving an actual plasma concentration of $10^{-7}$ M. The plasma is then incubated at 37° for 10 minutes, followed by addition of 8 ml heptane with 5% isoamylalcohol and extracted as above.

Each assay is run with a standard curve for the specific drug. Several known concentrations of drug (i.e., $3 \times 10^{-10}$, $10^{-9}$, $3 \times 10^{-9}$, $10^{-8}$) are placed in assay tubes instead of the ascorbic acid extracts and run as described below.

B. Receptor binding assay of plasma extracts.

(1) 100 μl of $^3$H-haloperidol (approximately 8000 CPM/100 μl) added to assay tubes.

(2) 100 μl of standard drug solutions added.

(3) 100 μl of plasma extracts (straight, 1:3, 1:10, or 1:30 dilution) added.

(4) Rat striatum tissue homogenized in 100 vols. of 0.05 M, Tris-HCl, pH 7.7 and centrifuged for 10 minutes at 15,000 g.

(5) Supernatant discarded. Pellet resuspended by sonication in 100 vols. of 0.05 M Tris pH 7.7 and recentrifuged for 10 min.

(6) Supernatant discarded. Pellet resuspended by sonication in buffer mix (Tris 7.7−7.5+ascorbic acid+pargyline+ions) (See Ex. 3 for amounts) to give a tissue concentration of 8 mg/ml.

(7) 0.8 ml of this homogenate added to tubes and incubated for 10 minutes at 37° C.

(8) Incubates filtered by vacuum through Whatman GF/B filters followed by 3 washes with the ice-cold Tris buffer.

(9) Filter, then put into plastic scintillation vials containing 9.0 ml of formula 947 (New England Nuclear) scintillation cocktail.

(10) Vials counted 2 minutes each.

(11) Values are read off a standard curve as in enclosed FIG. III.

EXAMPLE III

Thirty μl aliquots of patient plasma samples (previously frozen at −20° C.) from six patients undergoing haloperidol treatment were assayed in the radioreceptor assay with $^3$H-haloperidol as ligand according to a modification of Example I as follows: a standard curve of $^3$H-haloperidol displacement was constructed from known amounts of haloperidol in the presence of control plasma.

Fresh rat striatum was sonicated in 100 volumes (w/v) 50 mM Tris buffer, pH 7.7 at 25° C. with a Sonifier, setting 4 for 30 sec. The homogenate was centrifuged twice at 50,000×g for 10 min (Sorvall RC2-B) with rehomogenization of the intermediate pellet in fresh buffer. The final pellet was resuspended in 125 volumes of freshly prepared 50 mM Tris buffer containing 0.1% ascorbic acid, 10 μM pargyline, 120 mM NaCl, 5 mM KCl, 2 mM $CaCl_2$ and 1 mM $MgCl_2$ to give final pH of 7.1 at 27° C. The tissue suspension was preincubated at 37° C. for 10 min and returned to ice for use in the assay. $^3$H-Haloperidol (15 Ci/mmole, New England Nuclear) was diluted to 1 nM in fresh 0.1% ascorbic acid. Glass 12×75 mm incubation tubes received, in order, 15 μl plasma 100 μl $^3$H-ligand, 100 μl drug for standard curve or dopamine for blanks or the drug solvent to 0.1% ascorbic acid, and tissue suspension to 1 ml total volume. The tubes were incubated at 37° for 10 min and rapidly filtered under vacuum through Whatman GF/B filters with three 5 ml rinses of ice cold 50 mM Tris buffer, pH 7.7 at 25° C. $^3$H-Ligand trapped on the filters was counted by liquid scintillation spectrometry after remaining overnight in scintillation vials containing NEN formula 947 (New England Nuclear, Boston) or Hydromix fluor (Yorktown Laboratories). A standard displacement curve for the drug under study was determined in the presence of equal volumes of control plasma with final concentrations of the drug one-third, 3 times or the same as it Ki value determined previously. A log probit plot was used to convert the displacement curve to a straight line and percent inhibition of $^3$H-ligand binding was converted to molar drug concentration.

| Patient Samples | Dose level Haldol mg/day | Haloperidol ng/ml R.R.A. |
|---|---|---|
| 1 | 20 | 27 |
| 2 | 20 | 29 |
| 3 | 10 | 21 |
| 4 | 20 | 31 |
| 5 | 10 | 22 |
| 6 | 20 | 29 |

EXAMPLE IV

Five neuroleptic drugs were preincubated with serum for 10 min at 37° to provide time for binding to serum proteins and subsequently assayed for neuroleptic levels. Haloperidol (0.1 µM), fluphenazine (0.1 µM), trifluoperazine (0.1 µM), chlorpromazine (1 µM), and thioridazine (1 µM) were all fully recovered in the neuroleptin radioreceptor assay with respective values of 0.11±0.02 µM (n=6), 0.12±0.01 µM (n=10), 0.16±0.2 µM (n=6), 1.0±0.1 µM (n=9), and 1.1±0.2 µM (n=6). To examine the recovery of neuroleptic drugs from the blood of patients treated in vivo, blood levels in 4 patients receiving oral doses of haloperidol were measured both after extraction into organic solvent (heptane/5% isoamylalcohol, back extracted into 0.1% ascorbic acid) which should remove all drug bound to serum protein, and by adding serum directly to the binding assay as in the above method. Plasma drug levels ranged between 10 and 350 nM and agreed within a mean of 10% whether assays were conducted with or without extraction. This shows that, unexpectedly, neuroleptic drugs are loosely bound to plasma protein so that they are available for interaction with the dopamine receptor as needed in the present assay.

I claim:

1. The method of determining the concentration of neuroleptic drug and any active metabolites thereof in a body fluid containing same comprising (a) mixing together dopamine receptor material, radioactive dopamine receptor binder and body fluid, and measuring the amount of the radioactive dopamine receptor binder on the dopamine receptor material and (b) mixing together a concentration of a standard amount of non-radioactive dopamine receptor binder, dopamine receptor material and radioactive dopamine receptor binder and measuring the amount of radioactive dopamine receptor binder or the dopamine receptor material.

2. The method of claim 1 in which the material, binder, and body fluid are permitted to remain together a time sufficient to produce sufficient binding of the binder and drug and any active metabolites thereof in the body fluid to said receptor material prior to making the measurement.

3. The method of claim 1 in which the material, binder and body fluid are combined in the presence of sufficient buffer to produce a pH of about 6 to 9.

4. The method of claim 1 in which unbound binder and body fluid are removed as part of the measurement.

5. The method of claim 1 in which the dopamine receptor material is brain tissue, and the radionuclide portion of the binder comprises $^3$H or radioactive iodine.

6. The method of claim 1 in which iodine is $^{125}$I or $^{131}$I.

7. The method of claim 1 in which the concentration of body fluid in the mixture containing same is less than about 15%.

8. The method of claim 7 in which the concentration of body fluid in the mixture containing same is less than about 10%.

9. The method of claim 1 in which radioactive dopamine receptor binder is selected from the group of radioactive labelled, haloperidol, pimozide, chlorpromazine, fluphenazine, flupenthixol, spiroperidol, clazapine, thioridazine, fluspirilene, chopenthixol, loxapine, perphenazine, dopamine and apomorphine.

10. The method of claim 9 in which the radioactive receptor binder is radioactive labelled haloperidol.

11. The method of claim 9 in which the radioactive receptor binder is radioactive labelled spiroperidol.

12. The method of claim 1 in which measuring of the amount of radioactive dopamine receptor binder on the dopamine receptor material is determined in a gamma detector or scintillation counter based upon the nature of the radionuclide portion of the radioactive binder.

13. The method of claim 1 in which the concentration of drug and metabolite in the blood is determined by reference to a standard curve representing percent inhibition of radioactive dopamine receptor binder vs. non-radioactive dopamine receptor bind.

14. The method of claim 1 in which (b) is repeated a sufficient number of times while varying concentration of the non-radioactive binder to provide information for generating a standard curve.

15. The method of claim 14 in which the radioactive binder is the same in (a) and (b).

16. The method of claim 1 in which the receptor material is brain tissue.

17. The method of claim 1 in which the body fluid is blood plasma or blood serum.

18. The method of measuring the concentration of neuroleptic drug and any active metabolites thereof in blood plasma or blood serum containing same which comprises (a) mixing together blood plasma or blood serum with radioactive dopamine receptor binder and dopamine receptor material and measuring the amount of the radioactive dopamine receptor binder on the dopamine receptor material and (b) mixing together a concentration of a standard amount of non-radioactive dopamine receptor binder, dopamine receptor material and the same radioactive dopamine receptor binder as in (a) and measuring the amount of radioactive dopamine receptor binder on the dopamine receptor material.

19. The method of claim 18 in which measuring of the amount of radioactive dopamine receptor binder on the dopamine receptor material is determined in a gamma detector or scintillation counter based upon the nature of the radionuclide portion of the radioactive binder.

20. The method of claim 19 in which the concentration of drug and active metabolite is determined by reference to a standard curve representing percent inhibition of radioactive dopamine receptor binder vs. non-radioactive dopamine receptor binder.

21. The method of claim 18 in which unbound drug, unbound radioactive binder and plasma or serum are removed as part of determining the percent inhibition of binding.

22. The method of claim 18 in which the concentration of body fluid in the mixture containing same is less than about 15%.

23. The method of claim 22 in which the concentration is less than about 10%.

24. The method of claim 23 in which the amount of body fluid in the mixture containing same is greater than one microliter.

25. The method of claim 18 in which the receptor material is brain tissue.

26. The method of claim 18 in which (b) is repeated a sufficient number of times while varying concentration of the non-radioactive binder to provide information for generating a standard curve.

27. As a mercantile unit, a kit of at least one container of radioactive dopamine receptor binder, dopamine receptor material and standard non-radioactive dopamine receptor binder.

28. The kit of claim 27 in which the radioactive dopamine receptor binder is selected from the group consisting of radioactive labelled
pimozide,
chlorpromazine,
fluphenazine,
flupenthixol,
spiroperidol,
clozapine,
thioridazine,
trifluoperazine,
fluspirilene,
clopenthixol,
loxapine,
haloperidol, and
perphenazine.

29. The kit of claim 28 in which said standard binder is selected from the group consisting of,
pimozide
chlorpromazine
fluphenazine
flupenthixol
spiroperidol
clozapine
thioridazine
trifluoperazine
fluspirilene
clopenthixol
loxapine
haloperidol and
perphenazine.

* * * * *